US011219230B2

(12) United States Patent
Stürtz et al.

(10) Patent No.: US 11,219,230 B2
(45) Date of Patent: Jan. 11, 2022

(54) MIXTURES WITH STABILISING PROPERTIES

(71) Applicant: SYMRISE AG, Holzminden (DE)

(72) Inventors: Melanie Stürtz, Höxter (DE); Gerhard Krammer, Holzminden (DE); Günter Kindel, Höxter (DE); Birgit Kohlenberg, Pegestorf (DE); Marcus Eggers, Beverungen (DE); Nicole Schulze, Freden (DE); Julie Sicart, Vlaardingen (NL); Renske Tijssen, Vlaardingen (NL); Alessia Ermacora, Vlaardingen (NL)

(73) Assignee: SYMRISE AG, Holzminden (DE)

( * ) Notice: Subject to any disclaimer, the term of this patent is extended or adjusted under 35 U.S.C. 154(b) by 36 days.

(21) Appl. No.: 16/337,673

(22) PCT Filed: Nov. 24, 2017

(86) PCT No.: PCT/EP2017/080424
§ 371 (c)(1),
(2) Date: Mar. 28, 2019

(87) PCT Pub. No.: WO2018/096123
PCT Pub. Date: May 31, 2018

(65) Prior Publication Data
US 2019/0336423 A1    Nov. 7, 2019

(30) Foreign Application Priority Data

Nov. 25, 2016 (WO) ................ PCT/EP2016/078808

(51) Int. Cl.
| | | |
|---|---|---|
| *A23L 27/20* | (2016.01) | |
| *A23L 27/60* | (2016.01) | |
| *A23K 20/121* | (2016.01) | |
| *C12G 3/04* | (2019.01) | |
| *A21D 13/80* | (2017.01) | |
| *A23C 9/156* | (2006.01) | |
| *A61K 8/365* | (2006.01) | |
| *A61K 8/31* | (2006.01) | |
| *A61K 8/368* | (2006.01) | |
| *A61K 8/362* | (2006.01) | |
| *A61K 8/34* | (2006.01) | |
| *A61K 8/60* | (2006.01) | |
| *A61K 8/49* | (2006.01) | |
| *A61Q 1/14* | (2006.01) | |
| *A61Q 19/00* | (2006.01) | |
| *A23L 3/3481* | (2006.01) | |

(52) U.S. Cl.
CPC ............ *A23L 3/3481* (2013.01); *A21D 13/80* (2017.01); *A23C 9/156* (2013.01); *A23K 20/121* (2016.05); *A23L 27/2028* (2016.08); *A23L 27/2052* (2016.08); *A23L 27/60* (2016.08); *A61K 8/31* (2013.01); *A61K 8/345* (2013.01); *A61K 8/362* (2013.01); *A61K 8/365* (2013.01); *A61K 8/368* (2013.01); *A61K 8/498* (2013.01); *A61K 8/60* (2013.01); *A61Q 1/14* (2013.01); *A61Q 19/00* (2013.01); *A61Q 19/001* (2013.01); *C12G 3/04* (2013.01); *A23V 2002/00* (2013.01); *A61K 2800/522* (2013.01); *A61K 2800/5922* (2013.01)

(58) Field of Classification Search
CPC .... A23L 3/3481; A23L 27/60; A23L 27/2028; A23L 27/2052; A23K 20/121; A21D 13/80; A23C 9/156; A61K 8/31; A61K 8/362; A61K 8/365; A61K 8/368; A61K 8/498; A61K 2800/522; A61K 2800/5922; A61Q 1/14; A61Q 19/00; A61Q 19/001; C12G 3/04; A23V 2002/00
See application file for complete search history.

(56) References Cited

U.S. PATENT DOCUMENTS

| | | | | |
|---|---|---|---|---|
| 5,213,833 A | * | 5/1993 | Yamada | .................. A23B 4/20 |
| | | | | 426/542 |
| 2002/0176882 A1 | | 11/2002 | Schur | |
| 2003/0138537 A1 | * | 7/2003 | Bailey | .................. A23C 9/137 |
| | | | | 426/542 |

FOREIGN PATENT DOCUMENTS

| | | | | |
|---|---|---|---|---|
| JP | 2013176340 A | * | 9/2013 | |
| WO | 2008005548 A2 | | 1/2008 | |
| WO | 2013093730 A1 | | 6/2013 | |
| WO | WO-2015138479 A1 | * | 9/2015 | ............. A01N 31/14 |

OTHER PUBLICATIONS

Google scholar search—rosmarinic acid (Year: 2020).*
Translation JP2013176340 A from EPO (Year: 2020).*
International Search Report and Written Opinion dated Mar. 7, 2018 for corresponding PCT Application No. PCT/EP2017/080424.
Brewer, M.S., "Natural Antioxidants: Sources, Compounds, Mechanism of Action, and Potential Applications," Comprehensive Reviews in Food Science and Food Safety, vol. 10, No. 4, 2011, pp. 221-247.

(Continued)

*Primary Examiner* — Michael P Cohen
(74) *Attorney, Agent, or Firm* — Polsinelli PC

(57) ABSTRACT

The present invention primarily relates to novel mixtures with stabilizing properties, particularly for avoiding, reducing or delaying the formation of sensorially undesired flavours and/or tastes in oxidative degradation processes or autoxidative processes or reducing, avoiding or delaying oxidative processes in one or more oxidation-sensitive compounds, particularly autoxidative processes, their use in specific preparations as well as novel preparations and methods of producing such preparations. Additionally, herein described are methods for decreasing, avoiding or delaying the formation of sensorially undesired flavours and/or tastes in oxidative degradation processes or autoxidative processes or for decreasing, avoiding or delaying oxidative processes in one or more oxidation-sensitive compounds, particularly autoxidative processes.

19 Claims, No Drawings

(56) References Cited

OTHER PUBLICATIONS

Badee, A.Z.M. et al., "Improving the Quality and Self-Life of Refrigerated Chicken Meat by Marjoram Essential Oil," Journal of Applied Sciences Research, vol. 9, No. 11, 2013, pp. 5718-5729.

* cited by examiner

MIXTURES WITH STABILISING PROPERTIES

CROSS-REFERENCE TO RELATED APPLICATIONS

This application is a national stage application (under 35 U.S.C. § 371) of PCT/EP2017/080424, filed Nov. 24, 2017, which claims benefit of European Application No. PCT/EP2016/078808, filed Nov. 25, 2016, which are incorporated herein by reference in their entireties.

JOINT RESEARCH AGREEMENT

The inventions described and claimed herein were made pursuant to a Joint Research Agreement, in effect on or before the date the inventions were made, between Symrise AG and Conopco Inc., d/b/a UNILEVER.

The present invention primarily relates to novel mixtures with stabilising properties, particularly for reducing, delaying or avoiding the formation of sensorially undesired degradation products/compounds of oxidative processes (particularly for reducing, delaying or avoiding the formation of sensorially undesired flavours and/or tastes), particularly with oxidation-slowing or oxidation-inhibiting effect, their use in certain preparations, as well as novel preparations and methods of producing such preparations. The present invention further relates to methods for decreasing, avoiding or delaying the formation of sensorially undesired degradation products/compounds of oxidative processes (particularly for reducing, delaying or avoiding the formation of sensorially undesired flavours and/or tastes), particularly of autoxidative processes.

Further aspects of the present invention and preferred embodiments will arise from the following description and the enclosed patent claims.

Oxidative degradation processes and autoxidative processes play an important role for the sensorial stability of preparations, since they can destroy desired ingredients that then are no longer present or else undesired degradation products form that can produce unpleasant or undesired sensorial impressions. Ingredients that are often affected by this are, for example, flavouring substances that are of importance for the sensorial properties and the flavour, respectively, of a preparation and whose degradation and absence, respectively, usually negatively affects the overall sensorial impression of the preparation. The formation of the sensorially undesired degradation substances or compounds can be forced by the influence of warmth, that may occur, for example, during processing steps or during storage or transport as well as by the influence of light and UV irradiation, metal cations, air or certain enzymes, respectively. Further ingredients affected thereby are, for example, fats, oils, fatty acids, fatty acid esters and fatty acid derivatives, respectively, that are attacked and transformed or destroyed, respectively, by oxidative degradation processes and autoxidative processes. Substances that can produce an undesired flavour and/or an undesired taste in the preparation often are formed thereby. The sensorial properties and the flavor of a preparation, respectively, represent considerable quality features that may be the deciding factor for the purchase as well as the market.

The oxidative degradation of certain ingredients therefore often decreases the value of the product. This does not only affect food, but also, for example, cosmetics and pharmaceuticals. With these preparations it is particularly disadvantageous when unpleasant degradation products form and/or physical performance characteristics decrease because of oxidative degradation of the ingredients.

Document WO2013/189709A1 relates to a method of production of an EDTA-free mayonnaise by means of using a combination of reduced grape juice, acetic acid and proteins, whereby tartaric acid and malic acid as well as glucose and fructose are disclosed as components of the reduced grape juice. This described combination serves as EDTA-substitute and has oxidation-stabilising properties.

The article "Model Studies on the Antioxidant Activity of common Terpenoid Constituents of Essential Oils by Means of the 2,2-Diphenyl-1-picrylhydrazyl Method" by K. A. Woijtunik, L. M. Ciesla and M. Waksmundzka-Hajnos in the Journal of Agriculture and Food Chemistry (2014, 62, 9088-9094) discloses monoterpenes as antioxidants, particularly pulegone, citral, gamma-terpinene, myrcene and alpha-phellandrene.

US 2010/197812 A1 relates to compositions and methods for enhancing the stability of foods, beverages, nutritional supplements and cosmetics. An O/W emulsion is disclosed, in which the antioxidant is rosemary containing rosmarinic acid or combination of this with spent clove extract.

U.S. Pat. No. 4,963,385 relates to food emulsions containing highly unsaturated fatty acids or derivatives thereof, and that are stabilized against oxidative attack upon the unsaturated components by using a stabilizer system in the water phase of the emulsion which comprises either a sugar or sugar alcohol or a sugar or sugar alcohol (e.g. raffinose, trehalose, and sorbitol) and a metal-ion chelator (e.g. EDTA).

J. Sainsbury et al. (Food Chemistry, 213, 2016, p. 230-237) relates to the effects of levels of antioxidant (gallic acid or EDTA) in a sunflower oil salad dressing emulsion and shelf life affecting conditions on aroma, anisidine values (AV) and peroxide values (PV).

WO 2016/053971 A1 relates to a stabilized oil including an edible oil and an antioxidant composition comprising alpha-lipoic acid, and additionally at least one of ascorbic acid, ascorbyl palmitate, green tea extract, lecithin and rosemary extract.

US 2014/154377 A1 relates to stable oil-in-water emulsions comprising a polyunsaturated fatty acid, an emulsifier, water, a metal chelating agent, and an antioxidant. The metal chelating agent is selected from EDTA, citric acid, citrate, tartaric acid, ascorbic acid, phosphoric acid, a polyphenol, a pyrophosphate, a hexametaphosphate, whey, casein and combinations thereof. The antioxidant is selected from vitamin C, vitamin E (tocopherols), a polyphenol, a phenol derivative, carnosic acid, lipoic acid, taurine, an aromatic carboxylic acid, salts of an aromatic carboxylic acid, and combinations thereof.

F. Natella et al. (Journal Of Agricultural And Food Chemistry, 47(4), 1999, p. 1453-1459) relates to the antioxidant activity of four derivatives of benzoic acid and comparing this with the activity of the four homologous derivatives of cinnamic acid.

Further documents relating to or disclosing stabilizing or antioxidant activities of selected compounds are M. S. Brewer et al. ("Natural Antioxidants: Sources, Compounds, Mechanisms of Action, and Potential Applications", Comprehensive Reviews In Food Science And Food Safety, vol. 10, no. 4, 1 Jul. 2011, pages 221-247); US 2002/176882 A1; A. Z. M. Badee et al. ("Original Articles Improving the Quality and Shelf-Life of Refrigerated Chicken Meat by Marjoram Essential Oil", Journal Of Applied Sciences Research, vol. 9, no. 11, 1 Nov. 2013, pages 5718-5729); WO 2013/093730 A1 and WO 2008/005548 A2.

Common methods for counteracting oxidative degradation processes and autoxidative processes therefore are often based on the use of EDTA or antioxidants. Since the use of EDTA is regulated and only possible conditionally, there is an ongoing strong interest in alternative solutions to decrease or to avoid the oxidative degradation processes and autoxidative processes, respectively, and thereby the formation of substances causing undesired flavours and/or tastes and/or other disadvantageous effects (cf. above).

It was therefore the primary task of the invention to provide novel agents, particularly novel oxidation-slowing or oxidation-inhibiting or anti-autoxidative agents, with stabilizing properties that are suitable to decrease or to avoid undesired flavours and/or tastes that are formed or have formed during oxidative degradation processes and autoxidative processes or to slow down their formation and/or to retain the desired flavours and/or tastes and thereby to improve or to stabilize the sensorial durability and to overall improve the quality of flavoured preparations, respectively. Such agents preferably should be widely applicable so that they are not restricted to the use in specific preparations. Further details of this primary purpose, further problems underlying the present invention and individual or preferred aspects thereof will arise from the present description, the example section as well as particularly from the enclosed patent claims.

Within the scope of the present text, a stabilising property is preferably understood to be the property to slow down or to avoid altogether the change of substances during storage or processing or production of ingredients, in particular of ingredients and constituents of food and flavouring substances or to retain the formation of desired compounds.

Within the scope of the present text, an anti-autoxidative effect is preferably understood to be the property of chemical compounds or mixtures to slow down or to avoid altogether oxidative degradation processes and autoxidative processes of other substances, respectively.

The primary task of the present invention is solved by a mixture comprising or consisting of a) one or more monocyclic monoterpenes of formula (I)

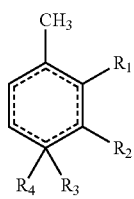

with R1=hydrogen, hydroxy group or carbonyl group, R2=hydrogen, hydroxy group or carbonyl group, R3=0 (according to one alternative, R3 is not present), hydrogen or hydroxy group and R4=isopropyl group, isopropenyl group or isopropylidene group as well as without or with one, two or three double bonds in the cyclic system, preferably selected from the group consisting of gamma-terpinene, alpha-terpinene, beta-terpinene, beta-phellandrene, limonene, thymol, pulegone, carvacrol and alpha-phellandrene, b) one or more benzoic acid derivatives of formula (II)

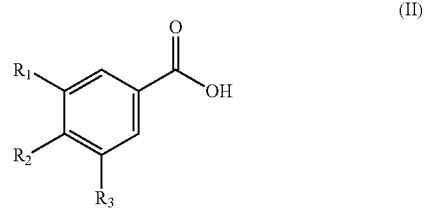

with R1, R2 and R3 independently of each other selected from the group consisting of hydrogen, hydroxy group and methoxy group, c) a first 3-phenylpropenoic acid derivative of formula (IV)

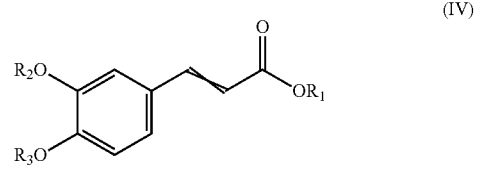

with R1=1-carboxy-2-(3,4-dihydroxyphenyl)ethyl, R2=hydrogen and R3=hydrogen, optionally a second 3-phenylpropenoic acid derivative of formula (IV) with R1=5-carboxy-2,3,5-trihydroxycyclohexyl, R2=hydrogen and R3=hydrogen, and optionally a third 3-phenylpropenoic acid derivative of formula (IV) with R1=hydrogen, R2=hydrogen and R3=hydrogen, or, respectively, 3-(3,4-dihydroxyphenyl)-2-[3-(3,4-dihydroxyphenyl)prop-2-enoyl]oxy-propionic acid, optionally 3-[3-(3,4-dihydroxyphenyl)prop-2-enoyl]oxy-1,4,5-trihydroxy-cyclohexane-1-carboxylic acid, and optionally 3-(3,4-dihydroxyphenyl)prop-2-enoic acid, d) tartaric acid (formula (V))

D-(−)-Form, and/or L-(+)-Form, and/or Meso-Form

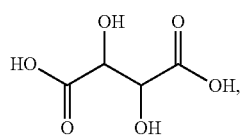

e) citric acid (formula (VI)) and/or malic acid (formula (VII))

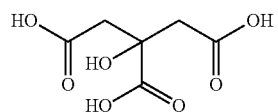

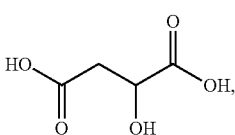

(VII)

f) glucose, fructose and/or sucrose,
g) 1,2-propanediol and/or 1,3-propanediol and/or propane-1,2,3-triol,
h) water,
i) optionally gallocatechin (Formula (III))

(2R,3S)-3,4-dihydro-2-(3,4,5-trihydroxyphenyl)-2H-1-benzopyran-3,5,7-triol

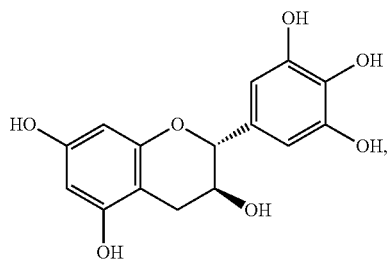

(III)

j) optionally one or more further flavouring substances, and
k) optionally one or more further solvents, preferably selected from the group consisting of triacetin (TRI), isopropanol (iPr), isopropyl myristate (IPM), ethanol, dipropylene glycol (DPG) and triethyl citrate (TEC), wherein the mixture comprises or consists of, with regard to the total weight of the mixture, respectively,
    0.0001 to 80 wt.-% of component a),
    0.0001 to 1.5 wt.-% of component b),
    0.0001 to 3 wt.-% of component c),
    0.005 to 10 wt.-% of component d),
    0.005 to 10 wt.-% of component e),
    0.000005 to 25 wt.-% of component f),
    0.0001 to 98 wt.-% of component g),
    0.0005 to 95 wt.-% of component h),
    0.0001 to 1 wt.-% of component i), if present,
    0.005 to 95 wt.-% of component j) if present, and
    0.01 to 95 wt.-% of component k), if present.

Such mixtures demonstrate particularly advantageous stabilizing properties and oxidation-decelerating, oxidation-inhibiting or anti-autoxidative effects, respectively, according to the studies carried out within the scope of the present invention. The mixtures according to the invention are particularly well suited to reduce or to avoid altogether undesired flavours and/or tastes that are formed or have formed by oxidative degradation and autoxidation, respectively, or to slow down their formation. Thereby, advantageously a better sensorial durability and stabilization of the preparation containing such substances can be achieved. Additionally, the mixtures according to the invention are thereby widely applicable, particularly as component of specific preparations containing one or more oxidation-sensitive compounds (as described herein). The individual substances of the mixture according to the invention are not able to slow down or to avoid altogether the formation of undesired flavours and/or tastes by oxidative degradation and autoxidation, respectively, over a longer period to the same extent as mixtures according to the invention are able to, so that less undesired degradation products are formed, that can produce unpleasant or undesired sensorial impressions.

Within the scope of the present invention it is preferred that the mixture according to the invention has an ORAC value of greater than 200 µmol TE/g, with respect to the dry weight of the mixture, preferably of greater than 500 µmol TE/g, particularly preferably of greater than 1000 µmol TE/g, especially preferably of greater than 2000 µmol TE/g.

ORAC stands for Oxygen Radical Absorption Capacity. The ORAC value determines the antioxidative ability or capacity of a substance or a mixture and is given in ORAC units (µmol TE/g) within the scope of the present text. The ORAC value therefore represents a characteristic measure of the antioxidative potential as is described in more detail in document WO2014147112 (A1).

According to a further preferred embodiment of the present invention the mixture has a polyphenol content according to Folin-Ciocalteu of greater than 5%, with respect to the dry weight of the mixture, preferably of greater than 10%, particularly preferably of greater than 15%.

The determination of the ORAC value and of the polyphenol content according to Folin-Ciocalteu took place during studies within the scope of the present invention and therefore also takes place within the scope of the present text generally following "Standardized Methods for the Determination of Antioxidant Capacity and Phenolics in Food and Dietary Supplements" by R. L. Prior, X. Wu and K. Schaich, Journal of Agriculture and Food Chemistry, 2005, 53, 4290-4302.

Because of their stabilising properties and oxidation-decelerating or oxidation-inhibiting or anti-autoxidative effects, respectively, the mixtures according to the invention are particularly well suited to reduce or to avoid undesired flavours and/or tastes (also known as off-tastes, off-flavours, off-notes, off-odours, bad scents, malodor, taste defects) that occur within the scope of oxidative and autoxidative processes or to slow down their formation. Such undesired off-notes are often described with terms such as, for example, rancid, roasty, nutty, bitter, pungent, poignant, scratchy, hay-like, chemical, technical, burnt, fatty, sour, herbaceous, stale, foul, fermented, aromatic, meaty, green, charred, fungal, smoky, buttery, vegetable-like, cooked, cheesy, carbonaceous, hot, fruity, metallic, dusty, spicy, powdery, sticky, floury or dry.

Preferred formulations of mixtures according to the invention comprise or consist of, respectively, components a) to h) as well as optionally i) to k) in the following amounts with regard to the total weight of the mixture, respectively:
    0.001 to 10 wt.-% of component a), preferably 0.01 to 5 wt.-%, particularly preferably 0.1 to 1 wt.-%,
    0.001 to 1 wt.-% of component b), preferably 0.005 to 0.25 wt.-%, particularly preferably 0.01 to 0.1 wt.-%
    0.001 to 1.5 wt.-% of component c), preferably 0.005 to 1 wt.-%, particularly preferably 0.01 to 0.7 wt.-%
    0.0075 to 5 wt.-% of component d), preferably 0.01 to 3 wt.-%, particularly preferably 0.01 to 0.5 wt.-%
    0.0075 to 8 wt.-% of component e), preferably 0.01 to 5 wt.-%, particularly preferably 0.01 to 3 wt.-%
    0.0000075 to 15 wt.-% of component f), preferably 0.00001 to 10 wt.-%, particularly preferably 0.00005 to 5 wt.-%, especially preferably 1 to 5 wt.-%, 0.0005 to 65 wt.-% of component g), preferably 0.001 to 45 wt.-%, particularly preferably 0.1 to 35 wt.-%

0.005 to 65 wt.-% of component h), preferably 0.01 to 50 wt.-%, particularly preferably 0.05 to 35 wt.-%

0.001 to 0.7 wt.-% of component i), preferably 0.005 to 0.5 wt.-%, particularly preferably 0.01 to 0.15 wt.-%

0.0075 to 50 wt.-% of component j), preferably 0.01 to 25 wt.-%, particularly preferably 0.05 to 15 wt.-%

0.05 to 65 wt.-% of component k), preferably 0.1 to 45 wt.-%, particularly preferably 1 to 35 wt.-%.

According to a preferred embodiment of a mixture according to the invention, the mixture is a flavor composition. Such mixture then regularly comprises the above-named component j), i.e. one or more further flavouring substances.

Flavouring substances in terms of the present invention preferably are substances that are defined by e.g. regulation (EG) No. 2232/96 of the European Parliament and Council and the positive list according to the implementing provision (EU) No. 872/2012 of the Commission, and the substances that are listed in "Riechstoffe" by Steffen Arctander, in "Perfume and Flavor Chemicals" published on his own, Montclair, N. J. 1969 as well as in "Common Fragrance and Flavor Materials" by H. Surburg, J. Panten, 5th Edition, Wiley-VCH, Weinheim 2006.

Examples for flavouring substances in terms of the present invention are saturated or unsaturated esters such as for example ethyl butyrate, benzyl acetate, methyl salicylate, neryl acetate, geranyl acetate, allyl capronate, anisyl acetate, anisyl formiate, butyl butyrate, butyl capronate, butyliden phthalide, cinnamyl acetate, benzyl benzoate, citronellyl acetate, cyclohexyl acetate, dimethyl anthranilate, ethoxyethyl acetate, ethyl butyrate, ethyl caprinate, ethyl capronate, ethyl crotonate, ethyl isobutyrate, ethyl isovalerianate, ethyl lactate, ethylmethyl butyrate, ethyl propionate, ethyl heptylate, methyldihydro jasmonate (e.g. Hedion®), cis-2-hexenyl acetate, cis-3-hexenyl acetate, cis-3-hexenyl capronate, trans-2-hexenyl capronate, cis-3-hexenyl formiate, cis-2-hexyl acetate, cis-3-hexyl acetate, trans-2-hexyl acetate, cis-3-hexyl formiate, isoamyl isovalerianate, isobutyl butyrate, linalyl acetate, methyl anthranilate, 2-methylbutyl acetate, methyl capronate, methyl cinnamate, methyl jasmonate, 2-methyl methylbutyrate, methylthio butyrate, 3-methylthio hexyl acetate, neryl acetate, 1-octyl acetate, 3-octyl acetate, phenylethyl acetate, phenylethyl isovalerianate, propyl butyrate, ethyl vanillin isobutyrate, acetic acid isoamyl ester, butyric acid ethyl ester, butyric acid n-butyl ester, butyrid acid isoamyl ester, 3-methyl-butyric acid ethyl ester, n-hexanoic acid ethyl ester, n-hexanoic acid allyl ester, n-hexanoic acid n-butyl ester, n-octanoic acid ethyl ester, ethyl-3-methyl-3-phenylglycidate, ethyl-2-trans-4-cis-decadienoate, methyl salicylate, methyl sorbate;

saturated or unsaturated organic acids such as for example butyric acid, acetic acid, methylbutyric acid, caproic acid, ethylbutyric acid, trans-2-hexenoic acid, trans-3-hexenoic acid, lauric acid, levulinic acid, 2-methyl-2-pentenoic acid, palmitic acid, valeric acid;

saturated or unsaturated alcohols such as for example octenol, cis-3-hexanol, benzyl alcohol, phenylethyl alcohol, eugenol, cis-3-hexenol, isoamyl alcohol, methyl butanol, 3,1-methylthio-hexanol, 2,4-nonadienol, 2,6-nonadienol, 2,4-nonadienol, 2-octanol, 3-octanol, 1,3-octenol, phenylethyl alcohol, cinnamyl alcohol;

saturated or unsaturated aldehydes such as for example acetaldehyde, isobutyric aldehyde, nonadienal, 3-phenylacetaldehyde, anisaldehyde, benzaldehyde, grapefruit aldehyde, heliotropin, trans-2-heptenal, cis-4-heptenal, trans-2-hexenal, 5-methylfurfural, trans,trans-2,4-Nonadienal, paraldehyde, piperonal, propionaldehyde, vanillin, ethylvanillin, acetoin, divanillin, phenylacetaldehyde, methional, (E,E)-2,4-decadienal, (E,E)-2,4-nonadienal, (E)-2-octenal, (E)-2-nonenal, 2-undecenal, 12-methyl tridecanal, cinnamic aldehyde;

ketones such as for example menthon, acetophenone, alpha-ionone, beta-ionone, damascone, 4-(p-hydroxyphenyl)-2-butanone, 2-heptanone, 3-heptanone, 4-heptanone, para-hydroxybenzyl acetone, 3,2,2-methyl cyclopentenolone, 6,5,2-methyl heptenone, nootkatone, pentandione, 4-(p-hydroxyphenyl)-2-butanone;

ethers such as for example 4-hydroxy-5-methyl furanone, 3-hydroxy-4,5-dimethyl-2-(5H)-furanone, 2,5-dimethyl-3-hydroxy-2(3H)-furanone, 2(5)-ethyl-4-hydroxy-5(2)-methyl-3(2H)-furanone, p-methoxybenzaldehyde, guajacol, methoxyvinyl phenol, ethyl furaneol, ethylguajacol, isoeugenol methyl ether, menthofuran, 2,5-dimethyl-4-hydroxy-3(2H)-furanond, homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone, 1,1-dimethoxy-2,2,5-trimethyl-4-hexane;

acetals such as for example acetaldehyde diethyl acetal;

lactones such as for example gamma-decalactone, dihydrocumarin, dodecalactone, nonalactone, methyl delta decalactone, massoia lactone, delta decalactone, tuberolactone;

terpenes such as for example linalool, citral, geranial, neral, menthol, cymol, myrcene, carene, cineol, sabinene, pinene-alpha, pinene-beta, citronellol, geraniol, terpineol, bisabolene, caryopyllene, farnesol, farnesene, carvone, camphene, citronellal, citral, eucalyptol, linalool oxide, menthol, nerol, phellandrene, pulegone, pulegol, sinensal, limonene, thymol, valencene, isopulegone;

sulfides and disulfides such as for example dimethyl sulfide, difurfuryl disulfide, methylthio propanal;

thiols such as for example methyl furanthiol, benzothiazole, isopropyl methyl thiazole, sulfurol, 8,3-thiomenthanone, 4,4,2-thiomethyl pentanone, 2,4,5-trimethyl thiazole, 2-acetylthiazole, 2,4-dimethyl-5-ethylthiazole;

pyrazines and pyrrolines such as for example methyl pyrazine, acetyl pyrazine, 2-propionyl pyrroline, 2-acetyl pyrroline, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-pentylpyridin;

as well as (not explicitly named herein) stereoisomers, enantiomers, positional isomers, diastereomers, cis/trans-isomers and epimers of these substances.

Flavouring substances can also directly influence the taste (taste modulators) and can be, for example, selected from the group consisting of monosodium glutamate, free glutamic acid, nucleotides or pharmaceutically acceptable salts thereof, strombines, theogallines such as described in JP 2007 110988 A, pyridine-betaine-compounds such as described in EP 1291342 B1, glutamic acid glycosides such as described in WO 2002 087361 A1, malic acid glycosides such as described in WO 2006 003107 A1, glutathion-derivates such as described in EP 0181421 or WO 2007 042273 A1, alkyl pyridines (preferably alkyl pyridines such as described in WO 2009 122318 A1 and WO 2009 1223319 A1), particularly 2-hexyl-, 2-heptyl and 2-octylpyridine, (2E,6Z)—N-cyclopropylnona-2,6-dienamide, (2E,6Z)—N-ethylnona-2,6-dienamide, N-[(2E)-3,7-dimethylocta-2,6-dienyl]cyclopropancarboxamide, N'-[(2-methoxy-4-methyl-phenyl)methyl]-N-[2-(5-methyl-2-pyridyl)ethyl]-oxamide, N'-[(2,4-dimethoxyphenyl)methyl]-N-[2-(2-pyridyl)ethyl] oxamide, N'-[(2-methoxy-4-methyl-phenyl)methyl]-N-[2-(2-pyridyl)ethyl]oxamide, N-(1-propylbutyl)-1,3-benzodioxole-5-carb-oxamide, 1-(2-hydroxy-4-isobutoxy-phenyl)-3-(2-pyridyl)propan-1-one and 1-(2-hydroxy-4-methoxy-phenyl)-3-(2-pyridyl)propan-1-one, cinnamic acid amides such as described in EP 2529632 B1 or WO 2013 000,673), lactisole, hesperitin according to EP 1909599 A1, phloretin according to EP 1972203 B1 or EP 1998636 B1, hydroxy-flavane according to US 2010 292175 AA, 4-hydroxychalcone according to EP 1972203 B1, extracts on the basis of *hydrangea dulcis* according to EP 2298084 A2, or *rubus* ssp.; mixtures of whey proteins with lecithines, yeast extracts, plant hydrolysates, pulverised vegetables (e.g. onion powder, tomato powder), plant extracts (e.g. of lovage or of mushrooms such as shiitake), seaweed and mineral salt mixtures, particularly mineral salt mixtures according to US 2009 214728 AA, rubemamine or rubescenamine according to EP 2529632 B1.

A preferred embodiment of a mixture according to the invention is a liquid form, particularly a form that can be incorporated into a preparation according to the invention (as described herein and further below).

Furthermore, a mixture according to the invention can also be transferred into a solid form, e.g. by means of spray drying, or can be present in solid form. Methods suitable therefore are sufficiently known to the skilled person.

As mentioned above, mixtures and flavouring compositions according to the invention, respectively, advantageously are suitable to be used in and incorporated into, respectively, a multitude of different preparations. Accordingly, the present invention also relates to a preparation, preferably a preparation for nourishment or pleasure, a preparation for animal feeding, a cosmetic preparation, a preparation for oral care or a pharmaceutical preparation for oral intake, comprising a mixture according to the invention as well as one or more further components.

Preferably, the or one, several or all of the components, respectively, are selected from the group consisting of oxidation-sensitive compounds, particularly such compounds that are sensitive towards autoxidation (cf. hereto above).

In light of the explanations above, it is of course particularly advantageous when the mixture according to the invention in the preparation according to the invention is comprised in an amount to reduce, avoid or delay the formation of sensorially undesired flavours and/or tastes in oxidative degradation processes or autoxidative processes or to reduce, avoid or delay oxidative processes in one or more oxidation-sensitive compounds, particularly autoxidative processes, and/or in an amount that is anti-autoxidatively effective. That is, (a) preferably the preparation has a higher Folin-Ciocalteu value than a preparation without the mixture according to the invention, but with an otherwise identical composition, and/or (b) preferably the amount of mixture according to the invention is sufficient to slow down or to reduce or to avoid altogether, respectively, oxidation or autoxidation, respectively, of one or more other substances comprised in the preparation (cf. hereto also example 2, comparison of the amount of formed degradation products).

In principle, what has been stated above with regard to preferred mixtures according to the invention also applies to mixtures preferably comprised in a preparation according to the invention. That is, a preparation according to the invention preferably comprises a mixture according to the invention that has been described above as preferred within the scope of the present invention.

Preferably, the total amount of mixture according to the invention in the preparation according to the invention is less than 5 wt.-%, preferably less than 3 wt.-%, particularly preferably less than 1 wt.-%, especially preferably less than 0.5 wt.-%.

For the production of a preparation according to the invention the required components can be mixed, whereby the components can be present in the form of solids, solutions, extracts, aqueous extracts as well as enriched preparations and concentrates, respectively, for example, by means of distillation, chromatography or Symtrap®. The Symtrap® method is a method of enrichment for the production of a flavour concentrate, which is described in document EP 2075321 B1.

The present invention also relates to a method of producing a preparation according to the invention, comprising or consisting of the following steps:
(i) provision of a mixture according to the invention, preferably of a mixture as described herein as preferred, or provision of the components a) to h) as well as optionally i), j) and k) of a mixture according to the invention, preferably of a mixture as described herein as preferred,
(ii) provision of one or more further components, and
(iii) mixing of the components provided in steps (i) and (ii).

According to a preferred embodiment, a preparation according to the invention is a preparation for nourishment or pleasure for example selected from baked goods (e.g. bread, dry biscuits, cake, other pastries), confectionery (e.g. chocolates, fillings, chocolate bar products, other bar products, candy, fruit gum, hard- and soft caramels, chewing gum), alcoholic and non-alcoholic beverages (e.g. coffee, tea, wine, wine-based beverages, beer, beer-based beverages, liqueurs, schnapps, brandy, fruit lemonades, isotonic beverages, soft drinks, nectars, fruit- and vegetable juices, fruit- and vegetable juice preparations), instant beverages (e.g. instant hot chocolate beverages, instant tea beverages, instant coffee beverages), solid or powdery instant products and instant spice mixes (e.g. spice mixes and stocks), liquid or paste-like spice mixes (e.g. meat stocks, concentrates, flavours, seasoning sauces), meat products (e.g. ham, fresh sausage- or raw sausage preparations, seasoned or marinated fresh- or salt meat products), eggs or egg products (dehydrated egg, egg white, egg yolk), cereal products (e.g. breakfast cereals, muesli bars, pre-cooked instant rice products), milk products (e.g. milk drinks, milk icecream, joghurt, kefir, cream cheese, soft cheese, hard cheese, dried milk powder, whey, butter, buttermilk, partly or fully hydrolysed milk protein-containing products), products made from soy protein or other soybean fractions (e.g. soy milk and products manufactured thereof, soy lecithin-containing preparations, fermented products such as tofu or tempe or products produced thereof, soy sauces), fruit preparations (e.g. jams, fruit icecream, fruit sauces, fruit fillings), vegetable preparations (e.g. ketchup, sauces, dehydrated vegetables, deep frozen vegetables, pre-cooked vegetables, vegetables marinated in vinegar, boiled down vegetables), snack articles (e.g. baked or deep-fried potato chips or potato dough products, bread dough products, extrudates, for example on corn- or peanut basis), products on fat- and oil basis or emulsions thereof (e.g. remoulade, mayonnaises, béchamel, hollandaise, aioli, mustard, chutneys, dips, sauces, dressings, spice preparations), other ready meals and soups (e.g. dried soups, instant soups, pre-cooked soups), spices, spice mixtures as well as particularly seasonings that, for example, are used in the snack area. The preparations according to the invention can also serve as intermediate goods for producing further preparations for nourishment or pleasure. The preparations according to the invention can also be present in the form of capsules, tablets (non-coated as well as coated tablets, e.g. with enteric coating), lozenges, granulates, pellets, solid mixtures, dispersions in liquid phases, as emulsions, as powders, as solutions, as pastes or as other swallowable or chewable preparations as dietary supplements.

According to a further preferred embodiment, a preparation according to the invention is a pharmaceutical preparation destined for oral intake, e.g. in the form of capsules, tablets (non-coated as well as coated tablets, e.g. with enteric coating), lozenges, coatings and swallowing aids for tablets and capsules, granulates, pellets, solid mixtures, dispersions in liquid phases, as emulsions, as powders, as solutions, as pastes or as other swallowable or chewable preparations and as pharmacy-only drugs, drugs available only on prescription, or other drugs or as dietary supplements.

According to another preferred embodiment, a preparation according to the invention is a preparation for oral care, e.g. selected from the group consisting of oral and/or dental care agents such as tooth pastes, tooth gels, tooth powders, mouthwashes, chewing gums and other oral care agents.

According to another preferred embodiment, a preparation according to the invention is a cosmetic preparation. Preferred cosmetic preparations within the scope of the present invention are in particular cosmetic preparations for application in the area of the head, preferably cosmetic preparations that can get in contact with the oral cavity even if applied correctly. Such preparations are, for example, soaps, other cleaning or care agents for the facial area, facial crèmes, -lotions or -ointments, sun protection agents, beard cleaning or care agents, shaving foams, -soaps or -gels, lip sticks or other lip cosmetics or lip care agents.

Preparations according to the invention can also comprise (other) common raw materials, excipients and additives, e.g.—in particular so for preparations serving nourishment or pleasure—(additional) water, mixtures of fresh or processed plant-based or animal-based raw materials (e.g. raw, fried, dried, fermented, smoked and/or cooked meat, bones, cartilage, fish, vegetables, fruits, herbs, nuts, vegetable- or fruit juices or -pastes or mixtures thereof), digestible or non-digestible carbohydrates, sugar alcohols (e.g. sorbit, erythritol), natural or hardened fats (e.g. tallow, lard, palm fat, coconut oil, hardened vegetable fat), oils (e.g. sunflower oil, peanut oil, corn oil, olive oil, fish oil, soy oil, sesame oil), fatty acids and salts thereof (e.g. potassium stearate), proteinogenic or non-proteinogenic amino acids and related compounds (e.g. gamma-amino butyric acid, taurine), peptides (e.g. glutathione), native or processed proteins (e.g. gelatin), enzymes and/or coenzymes (e.g. peptidases), nucleic acids, nucleotides, taste correctors or taste modulators, respectively, for unpleasant taste impressions or not unpleasant taste impressions, in particular taste-modulating substances (e.g. inositol phosphate, nucleotides such as guanosine monophosphate, adenosine monophosphate or other substances such as sodium glutamate or 2-phenoxypropionic acid), emulsifying agents (e.g. lecithins, diacylglycerols, gum arabic), stabilisers (e.g. carageenan, alginate), preservatives (e.g. benzoic acid, sorbic acid), further antioxidants, stabilisers, further organic or inorganic acidifying agents, bitter agents if applicable (e.g. quinine, caffeine, limonin, amarogentin, humolone, lupolone, catechins, tannins), sweeterners if applicable (e.g. saccharin, cyclamate, aspartame, neotame), mineral salts (e.g. sodium chloride, potassium chloride, magnesium chloride, sodium phosphate, calcium chloride), vitamins, substances avoiding enzymatic browning (e.g. sulfite, ascorbic acid), essential oils, plant extracts, natural or synthetic dyes or dye pigments (e.g. carotinoids, flavonoids, anthocyanes, chlorophyll and derivatives thereof), spices, trigeminally active substances or plant extracts comprising such trigeminally active substances, further synthetic, natural or nature-identical flavouring substances or aroma substances or fragrance substances as well as odour correctors.

Tooth care agents (as example for preparations according to the invention serving oral care; cf. above), usually comprise an abrasive system (abrasives or polishing agents), such as e.g. silicic acids, calcium carbonates, calcium phosphates, aluminum oxides and/or hydroxyapatites, surfactants such as e.g. sodium lauryl sulfate, sodium lauryl sarcosinate and/or cocamidopropylbetaine, humectants such as e.g. glycerine and/or sorbitol, thickening agents such as e.g. carboxymethyl cellulose, polyethylene glycols, carrageenans and/or Laponite®, sweeteners if applicable such as e.g. saccharin, taste correctors for unpleasant taste impressions or usually not unpleasant taste impressions, taste-modulating substances (e.g. inositol phosphate, nucleotides such as guanosine monophosphate, adenosine monophosphate or other substances such as sodium glutamate or 2-phenoxypropionic acid), cooling agents such as e.g. menthol, menthol derivates (e.g. L-menthol, L-menthyl lactate, L-menthyl alkyl carbonates, menthone ketals, menthane carboxylic acid amides), 2,2,2-trialkyl acetic acid amides (e.g. 2,2-diisopropyl propionic acid methylamide), icilin derivatives, stabilisers and active agents such as e.g. sodium fluoride, sodium monofluorophosphate, tin difluoride, quarternary ammonium fluorides, zinc citrate, zinc sulfate, tin pyrophosphate, tin dichloride, mixtures of different pyrophosphates, triclosan, cetylpyridinium chloride, aluminium lactate, potassium citrate, potassium nitrate, potassium chloride, strontium chloride, hydrogen peroxide, (further) flavours and/or sodium bicarbonate or odour correctors.

Chewing gums (as further or specific example, respectively, for preparations according to the invention serving oral care; cf. above), usually comprise a chewing gum base, that is a chewable base that becomes malleable during mastication, sugar of different kinds, sugar substitutes, sweeteners, sugar alcohols, taste correctors or taste modulators, respectively, for unpleasant taste impressions or usually not unpleasant taste impressions, taste-modulating substances (e.g. inositol phosphate, nucleotides such as guanosine monophosphate, adenosine monophosphate or other substances such as sodium glutamate or 2-phenoxypropionic acid), humectants, thickeners, emulsifiers, (further) flavours and stabilisers or odour correctors.

As further components for oral pharmaceutical preparations according to the invention (cf. above) mainly all of the commonly used active substances, raw materials, excipients, and additives can be used for pharmaceutical preparations provided for oral application. The active substances, raw materials, excipients, and additives can be transformed into application forms suitable for oral application according to known methods. This usually happens by means of using inert, non-toxic, pharmaceutically suitable excipients. This includes, amongst others, carrier substances (e.g. microcrystalline cellulose), solvents (e.g. liquid polyethylene glycols), emulsifiers (e.g. sodium dodecyl sulfate), dispersing agents (e.g. polyvinyl pyrrolidone), synthetic and natural biopolymers (e.g. albumin), stabilisers (e.g. antioxidants), dyes (e.g. inorganic pigments such as iron oxides) and odour correctors as well as taste correctors.

Preferably, preparations according to the invention (as described above) can contain a further flavor composition (not according to the invention) to (further) round off or refine the sensorial impression of the preparation. Suitable flavour compositions comprise e.g. synthetic, natural or nature-identical flavouring substances as well as suitable excipients and carrier substances.

From the above explanations in connection with the mixtures according to the invention described herein it becomes clear that they are also suitable for use as oxidation-decelerating or oxidation-inhibiting effective substance, particularly as anti-autoxidative effective substances. Particularly preferable is thereby the use of a mixture according to the invention in a preparation according to the invention (as described herein). It is thereby particularly advantageous, if the mixture according to the invention leads to (a) that the preparation comprising the mixture has a higher Folin-Ciocalteu value than a preparation without the mixture according to the invention, but with an otherwise identical composition, and/or (b) that the amount of mixture according to the invention (in the preparation) is sufficient to slow down or to reduce or to avoid altogether, respectively, an oxidation or autoxidation, respectively, of one or more other substances (comprised in the preparation) (cf. hereto also example 2, comparison of the amount of formed degradation products).

In this context, the present invention also relates to a method for reducing, avoiding or delaying the formation of sensorially undesired flavours and/or tastes in oxidative degradation processes or autoxidative processes or reducing, avoiding or delaying of oxidative processes in one or more oxidation-sensitive compounds, particularly autoxidative processes, comprising or consisting of the following steps:

(A) Provision of a mixture according the invention or provision of the components a) to h) as well as optionally i), j) and k) of a mixture according to the invention,
(B) provision of one or more further components, wherein the or one, several or all of the further components, respectively, is or are selected from the group consisting of oxidation-sensitive compounds, particularly those that are sensitive towards autoxidation, and
(C) contacting, preferably mixing, of the components provided in steps (A) and (B).
(cf. hereto also example 2, comparison of the amount of formed degradation products).

In terms of preferred embodiments of the method according to the invention, what has been stated above, in particular in connection with preferred embodiments of mixtures and preparations according to the invention, applies accordingly.

In the following, the present invention will be further described with the aid of selected, specific examples. The examples only serve to clarify the invention without limiting the invention or limiting it thereto. All specifications relate to the weight, unless indicated otherwise.

EXAMPLES

Example 1: Mixtures (According to the Invention

TABLE

| Mixture examples M1 to M6 | | | | | | | |
|---|---|---|---|---|---|---|---|
| Component | M1 wt.-% | M2 wt.-% | M3 wt.-% | M4 wt.-% | M5 wt.-% | M6 wt.-% | Supplier |
| Thymol | — | 0.1813 | 0.0001 | 0.0006 | 0.0002 | 0.0011 | Symrise |
| Limonene | 56.5544 | 0.5081 | 0.0098 | 0.0003 | 0.1013 | 0.0007 | MCI Miritz |
| gamma-Terpinene | 6.5319 | 0.1190 | 0.0012 | 0.0001 | 0.0909 | 0.0003 | Destillerias Munoz Galvez S. A. |
| Carvone | — | 0.4113 | 0.0032 | — | 0.0082 | 0.0001 | Sigma-Aldrich |
| Pulegone | — | 0.1496 | 0.0021 | — | 0.0023 | — | Berje Inc. |
| Carvacrol | — | 0.1889 | 0.0012 | 0.0002 | 0.0005 | 0.0001 | Frutarom |
| Gallic acid | 0.1221 | 0.6671 | 0.0076 | 0.0311 | 0.5110 | 0.0293 | Sigma-Aldrich |
| 4-Hydroxy-3,5-dimethoxybenzoic acid | — | 0.8211 | 0.0098 | 0.0047 | 0.8722 | 0.0046 | Alfa Aesar |
| Benzoic acid | — | 0.0097 | 0.0097 | — | 0.0083 | — | IMCD Deutschland |
| Gallocatechin | 0.1165 | 0.6161 | 0.4487 | 0.0054 | 0.3101 | 0.0053 | Sigma-Aldrich |
| 3-(3,4-dihydrogphenyl)prop-2-enoic acid | — | 0.0022 | — | 0.0057 | 0.0210 | 0.0061 | Sigma-Aldrich |
| 3-(3,4-dihydroxyphenyl)-2-[3-(3,4-dihydrogphenyl)prop-2-enoyl]oxy-propionic acid | 0.0112 | 1.3361 | 1.5030 | 0.5656 | 1.4211 | 0.5733 | Sigma-Aldrich |
| 3-[3-(3,4-dihydrogphenyl)prop-2-enoyl]oxy-1,4,5-trihydroxy-cyclohexane-1-carboxylic acid | — | 0.0001 | 0.1922 | — | 0.0022 | — | Sigma-Aldrich |
| Tartaric acid | 0.0550 | 5.5000 | 0.0115 | 2.0000 | 7.7010 | 2.1510 | UD Chemie |
| Citric acid | 1.8000 | 2.8500 | 0.0100 | 1.1000 | 3.8329 | 1.4377 | Sigma-Aldrich |
| Malic acid | 2.5000 | 3.3500 | 0.0103 | 1.1000 | 3.9412 | 1.3670 | UD Chemie |
| Glucose | 4.5112 | 7.5101 | 0.0029 | 5.0000 | 5.5000 | 4.9733 | Sigma-Aldrich |
| Fructose | 5.3831 | 8.8133 | 0.0026 | 6.6000 | 5.7000 | 6.4913 | Danisco |
| Sucrose | 0.0052 | 5.0220 | 0.0032 | 1.2000 | 1.1000 | 1.1798 | Nordzucker |

TABLE-continued

Mixture examples M1 to M6

| Component | M1 wt.-% | M2 wt.-% | M3 wt.-% | M4 wt.-% | M5 wt.-% | M6 wt.-% | Supplier |
|---|---|---|---|---|---|---|---|
| Water | 8.1126 | 25.0900 | 0.0550 | 15.0000 | 25.0000 | 50.6485 | |
| Propylene glycol | 14.2968 | 36.8540 | 97.7159 | 67.3863 | 43.8756 | 31.1305 | Dow |
| Sum | 100.0000 | 100.0000 | 100.0000 | 100.0000 | 100.0000 | 100.0000 | |

For production, the solid ingredients are solved in the premixed solvents water and PG. If necessary, this preparation is slightly heated to max. 40° C. until everything is solved. Then the other ingredients were added after cooling to room temperature.

Example 2: Dressing (A, B: Comparative Examples; C: According to the Invention

TABLE

Dressing

| Component | A wt.-% | B wt.-% | C wt.-% |
|---|---|---|---|
| Sunflower oil | 42.00 | 42.00 | 42.00 |
| Water | 25.26 | 25.16 | 25.16 |
| Egg yolk, pasteurised | 18.90 | 18.90 | 18.90 |
| Vinegar 5% | 5.91 | 5.91 | 5.91 |
| Mod. corn starch C*Tex06205 | 4.15 | 4.15 | 4.15 |
| Sucrose | 2.30 | 2.30 | 2.30 |
| Salt | 1.38 | 1.38 | 1.38 |
| Guar gum | 0.10 | 0.10 | 0.10 |
| Calcium-Disodium EDTA | — | 0.10 | — |
| Mixture M5 according to example 1 | — | — | 0.10 |
| Sum | 100.00 | 100.00 | 100.00 |

For production, the dry components are added to the water first and heated to 90° C., whereby this temperature is then kept for 3 minutes. Subsequently, the temperature is cooled to 25° C. and for sample B the EDTA and for sample C the mixture according to example 1 are added, respectively until everything is fully dissolved. Then the oil, the vinegar and the egg yolk are added. Subsequently, the preparations are homogenized with a high pressure homogenizer at 180 bar.

Stability Test:

Samples of preparations A, B and C were stored at 50° C. for 7 days in the heating cabinet to stimulate, to force and to investigate the oxidative and autoxidative processes, respectively.

Analytical Testing:

Analytical testing was carried out by means of Symstixx and GC-MS. A detailed description of the Symstixx® method is described in document EP 2233206 A1. The GC-MS measurement was carried out with a VF-Wax mx separating column (30 m×0.25 mm×0.25 mm) and a temperature program of 40° C.-3° C./min-230° C. During the measurements carried out, the substances hexanal, tr-2-octenal, 1,3-octenone, tr-2-heptenal, 2E,4Z-heptadienal, tr,tr-2,4-heptadienal, 2E-decenal, 2E,4E-decadienal, 2E,4E,7Z-decatrienal and 2E,4Z,7Z-undecatrienal that are typical for oxidative processes were determined. The determination of the amounts of these substances took place by means of the internal standard 2-nonanol. The determined ppm-amounts of these substances were summed up and the total amount of degradation substances was determined. The measured total amounts of sample A, sample B and sample C were compared to each other and the percentage ratio with regard to sample B was calculated.

TABLE

Results of the analytical measurements

| | A ppm | B ppm | C ppm |
|---|---|---|---|
| Total amount degradation substances | 16512 | 5791 | 3984 |
| percentage ratio in comparison with sample B | | | 31 |

The results show that sample A exhibits a considerably higher total amount of degradation substances than the other samples, wherein sample C with the mixture according to the invention displayed the lowest total amount of degradation substances. The measured total amount of degradation substances of sample C was 31% lower than the total amount of degradation substances of sample B with EDTA.

Example 3: Mayonnaise

TABLE

Mayonnaise

| Component | wt.-% |
|---|---|
| Sunflower oil | 79.20 |
| Water | 7.40 |
| Egg yolk, pasteurised | 6.00 |
| Vinegar 5% | 4.00 |
| Sugar | 1.50 |
| Table salt | 1.00 |
| Mixture M2 according to example 1 | 0.80 |
| flavour | 0.10 |
| Sum | 100.00 |

For production of the mayonnaise, the water, vinegar, sugar, salt, mixture M2 and flavour are mixed first. Then one third of this mixture is mixed with the egg yolk. To this mixture, the oil is added with a weak jet, slowly in the beginning and faster towards the end, with simultaneous strong emulsification work. In between and mainly towards the end, the remaining amount of the mixture of water, vinegar, sugar, salt, mixture M2 and flavor are added between two portions of oil.

Example 4: Seasoning

TABLE

| Cheese seasoning | |
|---|---|
| Component | wt.-% |
| Cheddar type cheese flavour SD | 2.00 |
| Citric acid | 0.30 |
| Lactic acid powder (loading 60% lactic acid) | 1.00 |
| Fat powder (Loading 77% fat) | 9.75 |
| Cheese powder mild cheddar type | 11.75 |
| Mixture M5 according to example 1 | 1.00 |
| Yeast extract powder | 5.00 |
| Salt for seasonings | 21.50 |
| Onion powder | 3.00 |
| Cream powder (43% fat) | 1.50 |
| Silicon dioxide | 0.70 |
| Curcuma extract in vegetable oil | 0.50 |
| Vegetable oil triglycerides/coconut oil | 0.30 |
| Lactose/milk sugar 100 mesh vegetarian | 20.00 |
| Glucose/Dextrose (Corn IP) | 8.00 |
| Wheat powder vegetarian | 13.70 |
| Sum | 100.00 |

First the crystalline substances are added to the liquid components and mixed until everything is uniform. Then the remaining dry components and the concentrates are added and mixed until everything is homogeneous.

Example 5: Milk Fat Filling

| Component | wt.-% |
|---|---|
| Dextrose | 10.00 |
| Icing sugar | 32.70 |
| Vegetable fat | 39.50 |
| Skim milk powder | 8.00 |
| Whole milk powder | 8.70 |
| Mixture M4 according to example 1 | 0.80 |
| Lecithin | 0.30 |
| Sum | 100.00 |

All components apart from half of the fat are mixed with each other. The refiner with three rollers should be used with a pressure setting of 60-75 bar for the input roller and of 110-125 bar for the output roller. Then the preparation is homogenized in the refiner. Subsequently, the remaining fat is introduced and mixed, respectively, with the aid of a mixer until the preparation is homogeneous.

Example 6: Biscuits

TABLE

| Biscuits | |
|---|---|
| Component | wt.-% |
| 1 Wheat flour type 550 | 48.45 |
| 2 Vegetable fat Bavetin 28090 LT | 19.50 |
| 3 Sugar | 19.50 |
| 4 Eggs | 5.00 |
| 5 Water | 5.00 |
| 6 Skim milk powder | 1.00 |
| 7 Mixture M1 according to example 1 | 1.00 |
| 8 Iodised salt | 0.30 |
| 9 Ammonium bicarbonate | 0.25 |
| Sum | 100.00 |

First, component No. 9 is dissolved in water and an elastic dough is formed from all of the components. Then the dough is cooled for 30 minutes and then rolled out to 2.75 mm. Subsequently, the dough is baked at 190° C. heat from above and at 200° C. heat from below for 8 minutes.

Example 7: Cracker

TABLE

| Cracker | |
|---|---|
| Component | wt.-% |
| Phase A | |
| 1 Wheat flour type 550 | 57.18 |
| 2 Wheat starch | 6.00 |
| 3 Glucose syrup C Sweet M 01415 | 6.00 |
| 4 Vegetable fat Biscuitine 200 | 10.00 |
| 5 Iodised salt | 1.00 |
| 6 Ammonium bicarbonate | 1.40 |
| 7 Baking powder | 0.30 |
| 8 Eggs | 5.00 |
| 9 Water | 13.00 |
| 10 Lecithin | 0.10 |
| 11 Enzyme Sternzym BK Quick | 0.02 |
| Phase B | |
| 1 Vegetable fat or vegetable oil | 98.90 |
| 2 Mixture M2 according to example 1 | 1.00 |
| 3 Aroma | 0.10 |
| Sum | 100.00 |

Phase A: First the ammonium bicarbonate is dissolved in water. Then the remaining components are mixed and then the mixture of water and ammonium bicarbonate is added. After the dough was kneaded in a Z-kneader for 6-8 minutes, it is brought to a temperature of 40° C. After a resting time of 30-60 minutes, the dough is rolled out to 1.75 mm and cut into 5×5 cm sized pieces. Then the pieces are baked at a heat from above of 300° C. and a heat from below of 260° C. for 3 minutes under steaming. After baking, the pieces are baked for a second time at a heat from above of 170° C. and a heat from below of 170° C. for 3 minutes and dried at 120° C. for 5 minutes. For production of phase B, the fat is melted, then the aroma and mixture M2 are added and homogenized. 8-10% of phase B are sprayed onto the dry crackers.

Example 8: Make-Up Remover

TABLE

Make-up remover

| Component | INCI | wt.-% |
|---|---|---|
| *Phase A* | | |
| Glycerin | Glycerin | 9.30 |
| Surfhope ® C-1216 | Sucrose Laurate | 3.00 |
| Surfhope ® C-1616 | Sucrose Palmitate | 3.00 |
| Water | Water (Aqua) | 4.70 |
| *Phase B* | | |
| Neutral oil | Caprylic/Capric Triglyceride | 47.71 |
| Dragoxat ® 89 | Ethylhexyl Isononanoate | 30.00 |
| Ionol CP | BHT | 0.05 |
| *Phase C* | | |
| Symdiol ® 68 | 1,2-Hexanediol, Caprylyl Glycol | 0.80 |
| *Phase D* | | |
| Perfume | Parfum | 0.15 |
| Mixture M3 according to example 1 | | 1.00 |
| Colour system I | Colour | 0.15 |
| Colour system II | Colour | 0.14 |
| Sum | | 100.00 |

The production takes place in a Becomix.

For production of phase A, the glycerin and Surfhope® C1216 are put into the Becomix and are stirred at −0.5 bar with 0.3 m/s, then they are homogenized with the aid of a Turrax at 3 m/s for 4 minutes. When the Surfhope® C1216 is completely dissolved, the Surfhope® C1616 is added, whereby the stirring is continued at 0.3 m/s. The subsequent homogenization takes place at 3 m/s for 4 minutes with the aid of a Turrax. Then water is added and again homogenized with the aid of a Turrax at 3 m/s for 6 minutes. This mixture is heated to 80° C. under stirring at 0.3 m/s, then brought to 50° C. and again homogenized with the aid of a Turrax with 3 m/s for 2 minutes. Subsequently, the temperature is raised to 80° C. and a pressure of −0.6 bar is adjusted.

The production of phase B takes place at 80° C. At a temperature of 80° C., the components of phase B are very slowly and consecutively mixed with each other and then stirred at 0.5 m/s as well as homogenized with the aid of a Turrax at 3 m/s for 2 minutes. When one quarter of the oil has been put into the boiler, a homogenization step takes place with the aid of a Turrax at 5 m/s for 4 minutes. After half of the oil has been added, it is homogenized again with the aid of a Turrax at 5 m/s for 4 minutes and the stirring speed is raised to 0.8 m/s. When three quarters of the oil have been added, a homogenization step with the aid of a Turrax at 5 m/s for 4 minutes and an increase of the stirring speed to 1 m/s follows. Then the remaining amount of the oil is added and stirred at 1.2 m/s.

After addition of phase C, the pressure is raised to −0.8 bar and it is homogenized with the aid of a Turrax at 5 m/s for 4 minutes. The preparation is cooled under stirring at 0.5 m/s to 25° C., whereby the stirring speed is reduced. Then phase D is added at 40° C.

Colour system I: 0.1% solution in isopropyl palmitate of D&C Red No 17 C.I. 26100

Colour system II: 0.1% solution in isopropyl palmitate of Phat Brown DC 8206: C.I. 47000, C.I. 26100, C.I. 60725

The final preparation has a viscosity of 69280 cP.

Example 9: Lip Care Stick

TABLE

Lip care stick

| Component | INCI | wt.-% |
|---|---|---|
| Medium mineral oil | Paraffinium Liquidum | 26.00 |
| Permulgin 3220 | Ozokerite | 20.00 |
| Paraffin 52-54 | Paraffin | 12.00 |
| Neutral oil | Caprylic/Capric Triglyceride | 9.95 |
| Mixture M1 according to example 1 | | 0.05 |
| Prisorine Sqs 3758 | Hydrogenated Polyisobutene | 5.00 |
| Cetiol 868 | Ethylhexyl Stearate | 5.00 |
| Softisan 100 | Hydrogenated Cocoglycerides | 5.00 |
| Xiameter ® PMX-0245 Cyclosiloxane | Cyclopentasiloxane | 4.00 |
| Elfacos E 200 | Methoxy PEG-22 and Dodecyl Glycol Copolymer | 4.00 |
| Permulgin 3430 | Copernicia Cerifera (Carnauba) Wax | 2.00 |
| Ivarlan 3360 | Glyceryl Lanolate | 3.00 |
| Super Hartolan | Lanolin Alcohol | 1.40 |
| Cutina ® FS 45 | Stearic acid, Palmitic acid | 1.50 |
| Jojoba oil | | 1.00 |
| Titanium dioxide | Titanium Dioxide | 0.10 |
| Perfume | Perfume | 0.01 |
| Sum | | 100.00 |

For production, all of the components in the order of the list without the perfume are melted and homogenized during warming to 70° C. At a temperature of 50° C., the perfume is added and homogenized.

Example 10: Night Cream

TABLE

Night cream

| Component | INCI | wt.-% |
|---|---|---|
| *Phase A* | | |
| Dragosan W/O P | Sorbitan Isostearate, Hydrogenated Castor oil, Beeswax (Cera Alba) | 5.00 |
| Medium Mineral Oil | Paraffinium Liquidum | 15.00 |
| Vaseline | Petrolatum | 4.50 |
| Tece Ozokerit N 325/II | Ozokerite | 2.30 |
| Dragoxat ® 89 | Ethylhexyl Isononanoate | 5.00 |
| *Phase B* | | |
| Water | Water (Aqua) | 64.10 |
| Glycerin, 99,5 P. | Glycerin | 3.00 |
| Magnesiumsulfate Heptahydrate | Magnesium Sulfate | 0.70 |
| Preservative Complex (ND Liquid) | Triethylene Glycol, Imidazolidinyl Urea, Methylparaben, Propylparaben, Dehydroacetic acid | 0.30 |
| *Phase C* | | |
| Perfume | Perfum | 0.10 |
| Mixture M3 according to example 1 | | 0.50 |
| Sum | | 100.00 |

For production, phase A and phase B are separately warmed to 80° C., respectively. Then phase B is added to phase A while using an Ultra-Turrax and emulsified. While stirring with a paddle agitator, this mixture is cooled and then emulsified again at 60° C. When the mixture has reached a temperature of about 35° C., phase C is added.

Example 11: Mayonnaise

TABLE

Mayonnaise

| Component | wt.-% |
|---|---|
| Sunflower oil | 79.20 |
| Water | 8.10 |
| Egg yolk, pasteurised | 6.00 |
| Vinegar 5% | 4.00 |
| Sugar | 1.50 |
| Table salt | 1.00 |
| Mixture M5 according to example 1 | 0.10 |
| flavour | 0.10 |
| Sum | 100.00 |

Example 12: M5 and Comparative Examples (Single Compounds) in Mayonnaise

Mayonnaises were prepared according to Example 11, wherein Mixture M5 was added or replaced in the same amount by one of the following single substances:

| Category in Claim 1 | Substance | Hexanal Fresh [ppb] | Stored [ppb] | %-increase |
|---|---|---|---|---|
| b) | Benzoic acid | 32.7 | 350.6 | 1072 |
| c) | 3-(3,4-dihydroxyphenyl)prop-2-enoic acid | 24.9 | 234.2 | 939 |
| a) | Carvone | 31.0 | 201.4 | 649 |
| c) | 3-[3-(3,4-dihydroxyphenyl)prop-2-enoyl]oxy-1,4,5-trihydroxy-cyclohexane-1-carboxylic acid | 27.0 | 277.0 | 1025 |
| e) | Citric acid | 23.2 | 151.4 | 653 |
| f) | Fructose | 32.9 | 334.1 | 1016 |
| b) | Gallic acid | 24.2 | 216.2 | 893 |
| j) | Gallocatechin | 22.4 | 213.0 | 950 |
| a) | gamma-Terpinene | 27.9 | 272.2 | 975 |
| f) | Glucose | 33.5 | 289.9 | 864 |
| a) | Limonene | 39.5 | 242.5 | 614 |
| e) | Malic acid | 23.9 | 215.1 | 902 |
| — | Mixture M5 | 24.7 | 148.1 | 600 |
| g) | Propylene glycol | 31.1 | 292.6 | 940 |
| a) | Pulegone | 37.7 | 218.4 | 579 |
| c) | 3-(3,4-dihydroxyphenyl)-2-[3-(3,4-dihydroxyphenyl)prop-2-enoyl]oxy-propionic acid | 21.9 | 117.8 | 538 |
| f) | Sucrose | 34.8 | 292.6 | 842 |
| b) | 4-Hydroxy-3,5-dimethoxybenzoic acid | 20.7 | 286.4 | 1381 |
| d) | Tartaric acid | 23.2 | 201.4 | 866 |
| h) | Water | 33.5 | 288.1 | 861 |

Stability test and analytical testing were performed as described above. The amount of Hexanal was analyzed in fresh mayonnaises and in stored mayonnaises as described above.

The experiments revealed surprising results. Supplementing mixture M5 with e.g. pure known antioxidants was expected to strongly inhibit the formation of Hexanal. However in the majority of experiments the single substances performed much worse than mixture M5. Only limonene, pulegone, and 3-(3,4-dihydroxyphenyl)-2-[3-(3,4-dihydroxyphenyl)prop-2-enoyl]oxy-propionic acid show a similar effect as the mixture M5. However, the pure substances were added in very high concentration for this kind of compounds, which would further make them unsuitable for use e.g. in food products. The off-taste that they would provide would be too high for such food products. E.g. limonene provides a very strong citrus flavour, and 3-(3,4-dihydroxyphenyl)-2-[3-(3,4-dihydroxyphenyl)prop-2-enoyl]oxy-propionic acid in pure form provides a very strong dry herbal, medicinal flavour; and pulegone provides a strong minty and camphor flavour. That makes these pure compounds not suitable to be used in a high concentration. The mixture of the invention solves this by using a combination of compounds, all in relatively low concentrations, and with a good antioxidative potential. Therewith the oxidation of the triglycerides can be effectively retarded, while still having a good-tasting product that does not have the off-taste associated with the same compounds in high concentrations.

Furthermore, it was surprising that e.g. sugars seem to have an impact on the production of Hexanal.

Moreover, even though terpenes are known for their stabilizing effect and for some an antioxidative effect is known, the use of terpenes as single substances replacing mixture M5 resulted in increased Hexanal formation.

Example 13: M5 and Comparative Examples (Mixtures) Used in Mayonnaise

Mayonnaises were prepared according to Example 11, wherein Mixture M5 was added or replaced in the same amount by one of the following mixtures:

| Category in claim 1 | Component | M5 | A | B | C | D | E | F |
|---|---|---|---|---|---|---|---|---|
| a) | Thymol | 0.0002 | 0.0000 | 0.0002 | 0.0002 | 0.0002 | 0.0002 | 0.0002 |
| a) | Limonene | 0.1013 | 20.0000 | 0.1155 | 0.1013 | 0.1013 | 0.1013 | 0.1013 |
| a) | gamma-Terpinene | 0.0909 | 0.0000 | 0.1036 | 0.0909 | 0.0900 | 0.0909 | 0.0909 |
| a) | Carvone | 0.0082 | 0.0000 | 0.0094 | 0.0082 | 0.0082 | 0.0082 | 0.0082 |
| a) | Pulegone | 0.0023 | 0.0000 | 0.0026 | 0.0023 | 0.0023 | 0.0023 | 0.0023 |
| a) | Carvacrol | 0.0005 | 0.0000 | 0.0006 | 0.0005 | 0.0005 | 0.0005 | 0.0005 |
| b) | Gallic acid | 0.5110 | 1.9000 | 0.5827 | 0.5110 | 0.5110 | 0.5110 | 0.5110 |
| b) | 4-Hydroxy-3,5-dimethoxybenzoic acid | 0.8722 | 0.0000 | 0.9945 | 0.8722 | 0.8722 | 0.8722 | 0.8722 |
| b) | Benzoic acid | 0.0083 | 0.0000 | 0.0095 | 0.0083 | 0.0083 | 0.0083 | 0.0083 |
| i) | Gallocatechin | 0.3101 | 0.0000 | 0.3536 | 2.0000 | 0.3101 | 0.3101 | 0.3101 |

-continued

| Category in claim 1 | Component | M5 | A | B | C | D | E | F |
|---|---|---|---|---|---|---|---|---|
| c) | 3-(3,4-dihydroxyphenyl)prop-2-enoic acid | 0.0210 | 0.0000 | 0.0239 | 0.0210 | 0.0210 | 0.0210 | 0.0210 |
| c) | 3-(3,4-dihydroxyphenyl)-2-[3-(3,4-dihydroxyphenyl)prop-2-enoyl]oxy-propionic acid | 1.4211 | 3.5000 | 1.6204 | 1.4211 | 1.4211 | 1.4211 | 1.4211 |
| c) | 3-[3-(3,4-dihydroxyphenyl)prop-2-enoyl]oxy-1,4,5-trihydroxy-cyclohexane-1-carboxylic acid | 0.0022 | 0.0022 | 0.0025 | 0.0022 | 0.0022 | 0.0022 | 0.0022 |
| d) | Tartaric acid | 7.7010 | 7.7010 | 8.7811 | 7.7010 | 7.7010 | 0.0000 | 7.7010 |
| e) | Citric acid | 3.8329 | 3.8329 | 4.3705 | 3.8329 | 3.8329 | 0.0000 | 3.8329 |
| e) | Malic acid | 3.9412 | 3.9412 | 4.4940 | 3.9412 | 3.9412 | 0.0000 | 3.9412 |
| f) | Glucose | 5.5000 | 5.5000 | 0.0000 | 5.5000 | 5.5000 | 5.5000 | 0.0000 |
| f) | Fructose | 5.7000 | 5.7000 | 0.0000 | 5.7000 | 5.7000 | 5.7000 | 35.0000 |
| f) | Sucrose | 1.1000 | 1.8189 | 0.0000 | 1.1000 | 1.1000 | 1.1000 | 0.0000 |
| h) | Water | 25.0000 | 15.0000 | 28.5063 | 25.0000 | 68.8765 | 25.0000 | 25.0000 |
| g) | Propylene glycol | 43.8756 | 31.1038 | 50.0292 | 42.1857 | 0.0000 | 59.3507 | 21.1756 |
| | Sum | 100.0000 | 100.0000 | 100.0000 | 100.0000 | 100.0000 | 100.0000 | 100.0000 |

Stability test and analytical testing were performed as described above. The amount of Hexanal was analyzed in fresh mayonnaises and stored mayonnaises as described above and is shown in the following table.

| Sample name | Hexanal fresh [ppb] | Stored [ppb] | %-increase |
|---|---|---|---|
| M5 | 31.6 | 98.5 | 311.3 |
| A | 29.7 | 98.6 | 331.7 |
| B | 23.9 | 107.0 | 448.4 |
| C | 27.5 | 81.8 | 297.1 |
| D | 26.6 | 83.4 | 313.7 |
| E | 31.2 | 106.3 | 341.0 |
| F | 27.7 | 104.8 | 378.2 |

Mixture M5 was selected exemplarily. Likewise the other mixtures according to the invention, see e.g. Example 1, could have been used.

Mixture A comprises high amounts of Limonene (component a)), Gallic acid (component b)) and 3-(3,4-dihydroxyphenyl)-2-[3-(3,4-dihydroxyphenyl)prop-2-enoyl] oxy-propionic acid (component c)). These substances are known as antioxidant agents. Even though the amounts of these substances are strongly reduced in mixture M5 and even the sums of components a), b) or c) are each lower in mixture M5 than in mixture A, the mixture according to the invention performs slightly better than mixture A, as a lower increase of the amount of Hexanal is observed. Such a result was not expected. Furthermore, high amounts of Gallic acid, 3-(3,4-dihydroxyphenyl)-2-[3-(3,4-dihydroxyphenyl)prop-2-enoyl]oxy-propionic acid and particularly Limonene increase the risk of generating undesired off-tastes as described above.

Mixture C comprises a strongly increased (almost 6-fold) amount of gallocatechin (component i)), which is known as a very potent antioxidant. However, mixture C and mixture M5 provide a comparable effect on the increase of Hexanal.

Mixture M5 performs comparable or even better than other mixtures with highly increased amounts of antioxidants but otherwise the same/similar composition. Such an effect was not expected, especially when the total amounts of known antioxidants were compared.

Compared to mixture D, mixture M5 comprises a solvent, Propylene glycol (component g)). Even though solvents may lead to an anti-synergistic effect of the respective components in a mixture, both mixtures achieve a comparable increase of the amount of Hexanal. Selecting Propylene glycol as a solvent resulted in no anti-synergistic effect. Furthermore, the solvent stabilizes the compounds in the mixture as well as in the emulsion system and mixture M5 comprising the solvent has a better solubility and can thus be added to the mayonnaise more easily.

Furthermore, mixture E comprises no tartaric acid (component d)), citric acid and malic acid (both component e)). When these substances are not included in the mixture, comparing mixture E and mixture M5, the increase of Hexanal is stronger. Thus, tartaric acid, citric acid and malic acid seem to improve the antioxidative/stabilizing properties, when they are added in a mixture.

Mixture B and mixture F do not comprise glucose and sucrose (both component f)). Further, mixture B does not comprise fructose (component f)), whereas mixture F contains a strongly increased amount of fructose compared to mixture M5. Both, mixture B and mixture F reveal a stronger increase of Hexanal production than mixture M5. Glucose, Fructose and Sucrose were not known to show an antioxidative effect. However, in the absence of these, or when fructose is strongly increased, less antioxidative effect is achieved and more Hexanal is produced, which was not expected. Furthermore, high amounts of sugars, as in mixture F, will negatively influence the viscosity of a mixture.

The results of these experiments demonstrate that the components need to be present in mixtures according to the invention and that these components are required in distinct concentrations. Substances with known antioxidative effect are not necessarily providing increased antioxidative effect when they are simply added to such mixtures in higher concentration.

The invention claimed is:
1. A mixture comprising:
   a) one or more monocyclic monoterpenes selected from the group consisting of gamma-terpinene, alpha-terpinene, beta-terpinene, beta-phellandrene, limonene, thymol, pulegone, carvacrol and alpha-phellandrene,
   b) one or more benzoic acid derivatives of formula (II)

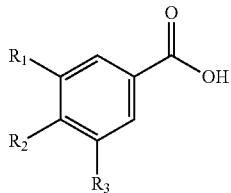

(II)

with R1, R2 and R3 independently of each other selected from the group consisting of hydrogen, hydroxy group and methoxy group,
   c) a first 3-phenylpropenoic acid derivative of formula (IV)

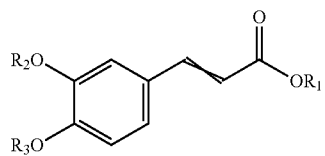

(IV)

with R1=1-carboxy-2-(3,4-dihydroxyphenyl)ethyl,
   R2=hydrogen and
   R3=hydrogen,
   optionally a second 3-phenylpropenoic acid derivative of formula (IV)
   with R1=5-carboxy-2,3,5-trihydroxycyclohexyl,
   R2=hydrogen and
   R3=hydrogen, and
   optionally a third 3-phenylpropenoic acid derivative of formula (IV)
   with R1=hydrogen,
   R2=hydrogen and
   R3=hydrogen,
   d) tartaric acid (formula (V))
   D-(−)-form, and/or L-(+)-form, and/or meso-form

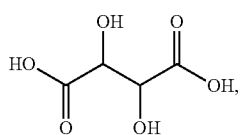

(V)

e) citric acid (formula (VI)) and/or malic acid (formula (VII))

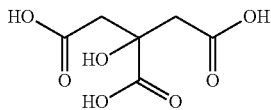

(VI)

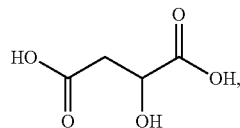

(VII)

f) glucose, fructose and/or sucrose,
   g) 1,2-propanediol and/or 1,3-propanediol and/or propane-1,2,3-triol,
   h) water,
   i) optionally gallocatechin (Formula (III))
      (2R,3S)-3,4-dihydro-2-(3,4,5-trihydroxyphenyl)-2H-1-benzopyran-3,5,7-triol

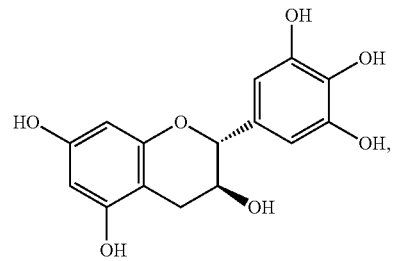

(III)

j) optionally, one or more further flavouring substances, and
   k) optionally, one or more further solvents,
      wherein the mixture comprises, with regard to the total weight of the mixture, respectively,
      0.0001 to 20 wt.-% of component a),
      0.0001 to 1.5 wt.-% of component b),
      0.0001 to 3 wt.-% of component c),
      0.005 to 10 wt.-% of component d),
      0.005 to 10 wt.-% of component e),
      0.000005 to 25 wt.-% of component f),
      0.0001 to 98 wt.-% of component g),
      0.0005 to 95 wt.-% of component h),
      0.0001 to 1 wt.-% of component i), if present,
      0.005 to 95 wt.-% of component j) if present, and
      0.01 to 95 wt.-% of component k), if present.

2. The mixture according to claim 1, wherein the mixture has an Oxygen Radical Absorption Capacity value of greater than 200 μmol Trolox Equivalents/g, with respect to the dry weight of the mixture.

3. The mixture according to claim 1, wherein the mixture has a polyphenol content according to Folin-Ciocalteu of greater than 5%, with respect to the dry weight of the mixture.

4. The mixture according to claim 1, comprising, with regard to the total weight of the mixture, respectively,
   0.001 to 10 wt.-% of component a),
   0.001 to 1 wt.-% of component b),
   0.001 to 1.5 wt.-% of component c),
   0.0075 to 5 wt.-% of component d),
   0.0075 to 8 wt.-% of component e),
   0.0000075 to 15 wt.-% of component f),
   0.0005 to 65 wt.-% of component g),
   0.005 to 65 wt.-% of component h),
   0.001 to 0.7 wt.-% of component i),
   0.0075 to 50 wt.-% of component j),
   0.05 to 65 wt.-% of component k).

5. The mixture according to claim 1, wherein the mixture is a flavour composition.

6. A preparation comprising a mixture according to claim 1 as well as one or more further components.

7. The preparation according to claim 6, wherein the or one, several or all of the further components, respectively, is/are selected from the group consisting of oxidation-sensitive compounds.

8. The preparation according to claim 6, wherein the mixture is contained in the preparation in an effective amount to reduce, avoid or delay the formation of sensorially undesired flavours and/or tastes in oxidative degradation processes or autoxidative processes or to reduce, avoid or delay oxidative processes in one or more oxidation-sensitive compounds.

9. The preparation according to claim 6, wherein the total amount of mixture in the preparation, with regard to the total weight of the preparation, is less than 5 wt.-%.

10. The mixture according to claim 1 having an Oxygen Radical Absorption Capacity value of greater than 500 µmol Trolox Equivalents/g, with respect to the dry weight of the mixture.

11. The mixture according to claim 1 having an Oxygen Radical Absorption Capacity value of greater than 2000 µmol Trolox Equivalents/g, with respect to the dry weight of the mixture.

12. The mixture according to claim 1 comprising the one or more further solvents of k), wherein the one or more further solvents of k) are selected from the group consisting of triacetin (TRI), isopropanol (iPr), isopropyl myristate (IPM), ethanol, dipropylene glycol (DPG), and triethyl citrate (TEC).

13. The mixture according to claim 1, comprising, with regard to the total weight of the mixture, respectively,
   0.01 to 5 wt.-% of component a),
   0.005 to 0.25 wt.-% of component b),
   0.005 to 1 wt.-% of component c),
   0.01 to 3 wt.-% of component d),
   0.01 to 5 wt.-% of component e),
   0.00001 to 10 wt.-% of component f),
   0.001 to 45 wt.-% of component g),
   0.01 to 50 wt.-% of component h),
   0.005 to 0.5 wt.-% of component i),
   0.01 to 25 wt.-% of component j),
   0.1 to 45 wt.-% of component k).

14. The mixture according to claim 1, comprising, with regard to the total weight of the mixture, respectively,
   0.1 to 1 wt.-% of component a),
   0.01 to 0.1 wt.-% of component b),
   0.01 to 0.7 wt.-% of component c),
   0.01 to 0.5 wt.-% of component d),
   0.01 to 3 wt.-% of component e),
   0.00005 to 5 wt.-% of component f),
   0.1 to 35 wt.-% of component g),
   0.05 to 35 wt.-% of component h),
   0.01 to 0.15 wt.-% of component i),
   0.05 to 15 wt.-% of component j),
   1 to 35 wt.-% of component k).

15. The mixture according to claim 1, wherein the mixture has a polyphenol content according to Folin-Ciocalteu of greater than 10%, with respect to the dry weight of the mixture.

16. The mixture according to claim 1, wherein the mixture has a polyphenol content according to Folin-Ciocalteu of greater than 15%, with respect to the dry weight of the mixture.

17. The mixture according to claim 1 comprising the (2R,3S)-3,4-dihydro-2-(3,4,5-trihydroxyphenyl)-2H-1-benzopyran-3,5,7-triol.

18. A method of producing a preparation according to claim 6, comprising:
   (i) providing components a) to h) as well as optionally i), j) and k) of the mixture,
   (ii) providing one or more further components, and
   (iii) mixing of the components provided in (i) and (ii).

19. A method for reducing, avoiding or delaying the formation of sensorially undesired flavours and/or tastes in oxidative degradation processes or autoxidative processes or reducing, avoiding or delaying of oxidative processes in one or more oxidation-sensitive compounds:
   (A) providing a mixture according to claim 1 or providing the components a) to h) as well as optionally i), j) and k),
   (B) providing one or more further components, wherein the further components, respectively, is/are selected from the group consisting of oxidation-sensitive compounds, and
   (C) mixing the components provided in steps (A) and (B).

* * * * *